United States Patent [19]

Schwartz et al.

[11] Patent Number: 4,486,222
[45] Date of Patent: Dec. 4, 1984

[54] HERBICIDE COMPOSITION AND PROCESS FOR THE PREPARATION OF THE ACTIVE INGREDIENTS HERBICIDAL PHENYL CARBONATES

[75] Inventors: Jozsef Schwartz; Marya Hornyak nee Hamori; Janos Sagi, all of Budapest; Katalin Marmarosi nee Kellner, Biatorbágy; Erzsebet Radvanyi nee Hegedus, Budapest; Zoltan Szigeti, Budapest; Edit Cseh, Budapest; Klara Bujtas nee Tolgyes, Budapest, all of Hungary

[73] Assignee: Chinoin Gyogyszer es Vegyeszeti Termekek Gyara Rt., Budapest, Hungary

[21] Appl. No.: 469,301

[22] Filed: Feb. 24, 1983

[30] Foreign Application Priority Data

Apr. 28, 1982 [HU] Hungary .............................. 1340/82
Apr. 28, 1982 [HU] Hungary .............................. 1341/82

[51] Int. Cl.³ ..................... A01N 37/34; C07C 121/75
[52] U.S. Cl. ........................................ 71/100; 71/105;
260/455 B; 260/463; 260/465 D
[58] Field of Search .............. 260/463, 465 D, 455 A, 260/455 B; 71/105, 100

[56] References Cited

U.S. PATENT DOCUMENTS 3,329,702 7/1967 Rohr ................. 260/465 D
3,480,658 11/1969 Rohr ................. 260/465 D
3,592,626 7/1971 Heywood et al. ........ 71/105 X
3,641,062 2/1972 Ost et al. .............. 71/105 X

FOREIGN PATENT DOCUMENTS 1375311 9/1964 France .
154690 11/1968 Hungary .
1067032 4/1967 United Kingdom .

OTHER PUBLICATIONS

Chemical Abstracts, vol. 62, 3982-3983, (1965).

Primary Examiner—Dolph H. Torrence
Attorney, Agent, or Firm—Karl F. Ross

[57] ABSTRACT

New herbicidal compounds of the formula (I)

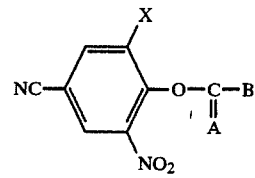

wherein
A is oxygen or sulfur;
B is $O-C_1$ to $C_4$ alkyl, $O-C_2$ to $C_6$ alkenyl, $O-C_6$ to $C_{10}$ aryl, $O-C_1$ to $C_4$-alkoxy-$C_1$ to $C_4$ alkyl, $S-C_1$ to $C_4$ alkyl or dimethylamino; and
X is chloro, bromo or iodo, are disclosed, as well as herbicidal compositions containing said compounds.

10 Claims, No Drawings

HERBICIDE COMPOSITION AND PROCESS FOR THE PREPARATION OF THE ACTIVE INGREDIENTS HERBICIDAL PHENYL CARBONATES

The invention relates to a postemergent herbicide composition and to a process for the preparation of the active ingredients.

The active ingredients of the herbicide composition according to the present invention can be characterized by the formula II

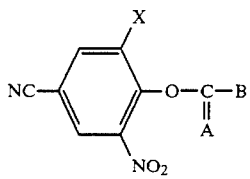

In the formula II
A stands for oxygen or sulphur,
B stands for an O-alkyl-, O-alkenyl-, O-aryl-, O-alkoxy-alkyl or a dimethylamino group,
X stands for a chlorine, bromine or iodine atom.

The aryl group contains 6–10 carbon atoms and it is advantageously a phenyl group, the alkenyl group contains 2–6 carbon atoms and is advantageously an allyl group, the alkyl-, and alkoxy group, respectively may contain 1–4 carbon atoms.

Compounds of the formula I

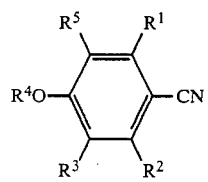

which are the nearest to the active ingredients of the formula II of the herbicide compositions according to the present invention are set forth in the Hungarian Patent Specification No. 154.690.

In the formula I
$R^1$ and $R^2$ are identical or different and mean a hydrogen or halogen atom,
$R^3$ is a halogen atom,
$R^4$ is a hydrogen atom, an acyl- or alkoxycarbonyl group, an alkali metal, or earth alkali metal, an ammonium ion or an organic amino group,
$R^5$ is a hydrogen or halogen atom, or a nitro group, with the proviso that amongst $R^1$, $R^2$ and $R^5$ at least one is and at most two are a hydrogen atom, with the further proviso, that (1) when $R^1$ and $R^2$ are a hydrogen atom and $R^3$ and $R^5$ are iodine atoms, $R^4$ can not represent a hydrogen atom, an acetyl group, a sodium or potassium atom and (2) when $R^1$ and $R^2$ are hydrogen atoms and $R^3$ and $R^5$ both represent a bromine or chlorine atom, $R^4$ can not represent a hydrogen atom, an acetyl group or a sodium atom.

We have found that the compositions according to the present invention, containing the compounds of the formula II can be fairly applied postemergently for the selective extirpation of weeds because the phytotoxic action of the active ingredients of the formula II exerted on the monocotyledonous and dicotyledonous plants is different. The active ingredients of the formula II, when postemergently applied in a dose of 2–4 kg/ha are damaging the monocotyledonous plants on an average of 15–25%, and the dicotyledonous plants on an average of 70–85%.

The known 3,5-dibromo-4-hydroxy-benzonitrile (Bromoxinyl) of the formula I, its octane acid ester respectively (Brominal) is damaging at the same time the monocotyledonous plants in a very large extent (77%), but the dicotyledonous plants nearly in the same extent (89%) too.

According to the teaching of the Hungarian Patent Specification No. 154.690 the active ingredients of the formula I can be applied only in a dose of 0.28–0.56, at most in a dose of 0.56–1.68/ha without damaging the cultivated plants, at the same time 2,24–4.48 kg/ha of the active ingredients of the formula I.are wanted to achieve the total weed control effect.

The active ingredients of the formula II. according to the present invention can be applied in a dose of 7.0 kg/ha too in the weed control of maize without damaging the cultivated plants.

We have further found, that the active ingredients of the formula II are extirpating better the triazine-resistent Amaranthus and Chenopondium species-causing a continually increasing trouble in the maize cultures-, than the known Brominal. The effectiveness tests on small parcels by treating maize stocks were carried out as follows:

Sowing was preceded by 25–32 cm ploughing and harrowing, basic treatment with weed control was not applied.

The postemergent treatment was applied in the one month state of maize with a water amount of 300 l/ha and with active ingredient doses of 0,5–1.0–1,5 kg/ha. For the treatment the following composition was applied:

| | |
|---|---|
| (2-bromo-4-cyano-6-nitro-phenyl)-methyl carbonate of formula II.a. | 80% |

II.a.

CH₃O—COO—[Br, CN, NO₂ substituted benzene ring]

| | |
|---|---|
| sodium salt of the alkylnaphthalene sulphonic acid (Wettol NT 1) | 3% |
| sodium salt of the lignin sulphonic acid (Borresperse) | 5% |
| silicon dioxide (Neuburg chalk) | 12% |

Atomization was carried out with Tee-Jet 11008–11010 nozzles at a pressure of 2.0–2.5 atmospheres. As a standard the formulated composition of 3,5-dibromo-4-hydroxy-benzonitrile-octanoate (active ingredient B)(Brominal 32 EC) was applied in an amount of 0.66 kg/ha. The state of evolution of the prevalent weeds at the period of treatment was as follows:

| | |
|---|---|
| 1. *Amaranthus retroflexus* | 20 cm |
| 3. *Chanopodium album* | 15–20 cm |
| 2. *Amaranthus chlorostachys* | 20 cm |
| *Hibiscus trionum* | 4–6 cm |

-continued

| | |
|---|---|
| Stachys annua | 4–8 cm |
| Malva neglecta | 4–6 leafy |

The evaluation carried out 10 days after the treatment is shown in table 1. Brominal applied as a standard caused slight phytotoxic symptoms on the maize.

The evaluation was carried out according to the EWEC scale. Accordingly value 1 means an excellent (100%), 2 a very good (98%), 3 a good (95%), 4 a satisfactory (90%), 5 a problematical (82%), 6 an insufficient (70%), 7 a bad (55%), 8 a very bad (30%) and 9 means a useless (0%) weed control.

TABLE I

| Active ingredient | dose kg active ingr. per ha | A. recto-flexus | A. Chlo-rostachys | C. album | I. tri-onum | S. an-nua | M. neg-lecta |
|---|---|---|---|---|---|---|---|
| B | 0.66 | 5 | 6 | 3 | 5 | 6 | 4 |
| II. a. | 0.5 | 3 | 4 | 2 | 3 | 6 | 4 |
| | 1.0 | 2 | 2 | 1 | 3 | 4 | 3 |
| | 1.5 | 2 | 2 | 1 | 3 | 4 | 3 |

The active ingredients according to the present invention of the formula II are further suitable to the postemergent weed control of numerous vegetables-e.g. of peas, onions, carrots, etc. too.

With the preparation of the following composition the activity test was carried out in a green house.

| | |
|---|---|
| (2-bromo-4-cyano-6-nitro-phenyl)-allyl carbonate of formula II/b | 80% |

II/b $$\underset{NO_2}{\underset{|}{\underset{\displaystyle\bigcirc}{NC-}}}\text{—}\overset{Br}{\underset{\displaystyle\bigcirc}{}}\text{—}O\overset{O}{\underset{\|}{C}}-O-CH_2-CH=CH_2$$

| | |
|---|---|
| sodium salt of the alkylnaphtalene sulphonic acid (Wettol NT 1) | 3% |
| sodium salt of the lignin sulphonic acid (Borresperse) | 5% |
| silicon dioxide (Neuburg chalk) | 12% |

As a standard the formulated composition of 3,5-dibromo-4-hydroxy-benzonitrile-octaneate (active ingredient B) (Brominal 32 EC) was applied.

The results are shown in example No. 6.

Detailed laboratory experiments were carried out to establish wether differences between the activity and selectivity of the compounds according to the present invention and of Bromoxinyl observed in free soil experiments are manifesting themselves on the level of action mechanisme and mode of action too.

We examined the effect of the compounds on the activity of the photo synthesis, because from the dihalogen substituted hydroxy-benzonitrile herbicides it is taken for granted that their primary attacking point is in the photosynthetic electron transport chain. We extended out investigations on the examination of the simple lengthening (growing) process and of the membrane function (active K+-influx electrolyte efflux).

In the growth test (lengthening of the lettuce bud plant root) we have stated that the dibromo derivatives are showing a similar activity to the growth controlling plant hormones: in a low concentration they stimulate the lengthening of the root and in higher concentrations they are sturdily inhibiting the same.

Up to the present a similar growth controlling activity was only shown by the Bromoxinyl esters of type 2,4-D (Heywood 1966 Chem. and Ind. 1946–1952). The effect of the (2-bromo-4-cyano-6-nitrophenyl)-alkali carbonates in the lettuce root lengthening is of another character, after the initial ineffectiveness inhibition is experienced, the growth stimulation does not take place (see example No.3).

Comparing the results of the growth and membrane function tests we can conclude that the cause of the differences between the biological action spectrum of the compounds of the present invention and of the herbicides known up to the present is that their getting into the plant and their translocation in the same is different.

From the photosynthetic activity test of monocotyledonous and dicotyledonous test plants (wheat and spinach) based on dichlorophenol-indophenol (DCPIP)-reduction measured on intact plants with in vivo CO-fixation and isolated chloroplastics we could establish the following facts. The dibromo-substituted compound is acting equally sturdily on dicotyledonous plants and moderately on monocotyledonous plants in a smaller extent than Bromoxinyl (see example No.3.).

In the laboratory tests for the measurement of the activity of the photo-synthesis the selectivity of the bromo-nitro substituted compounds was greater between the mono- and dicotyledonous plants than that of the dibromo compounds.

The active ingredients of the formula II are applied in the plant protection in the form of compositions-wettable powder composition, paste, emulsion concentrate, etc. The compositions may contain besides the active ingredient solid or liquid carriers or diluents, surface active agents and further auxiliary products.

The active ingredient content of the compositions can be 0.1–90 w%. The compositions are diluted on the area of application to the required active ingredient content.

A further subject of the invention is a process for the treatment of maize, grain and vegetable cultures for postemergent weed control.

According to the invention one proceeds in a way, that in the above mentioned cultures the weed control is carried out postemergently with a composition containing 0,1–90 w% of the active ingredient of the forumula II in a dose of 1–4 kg active ingredient/ha.

The compounds of the formula II according to the invention can be prepared in a way that a compound of the formula III

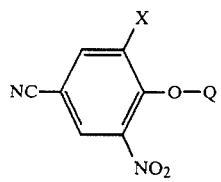

wherein Q is a tertiary base and X is a chlorine-, bromine- or iodine atom-is reacted with a carbonic acid derivative of the formula IV

wherein the meaning of A and B are the same as set forth above and that of Z is a chlorine or bromine atom.

The reaction is carried out advantageously in a solvent medium at a temperature between 20°–60° C.

The invention is illustrated by the following examples without limiting the same to the examples.

EXAMPLES

1. Preparation of (2-bromo-4-cyano-6-nitro-phenyl)-methyl-carbonate 121,5 g of 3-bromo-4-hydroxy-5-nitro-benzonitrile are dissolved in 650 ml of benzene and 73 ml of triethylamine are added. The solution obtained is reacted with a solution of 44 ml of chloro-formic acid methylester in 75 ml of benzene in about 30 minutes (dropwise) at 20°–25° C. Thereafter the mixture is stirred at 20°–25° C. for 2 hours and further at 55°–60° C. for 1 hour, cooled and 100 ml of water are added. After separation of the layers the benzene solution is washed with another 100 ml of water. The washing water is once extracted with 50 ml of benzene. The unified benzene solution is dried with anhydrous sodium sulphate and clarified with charcoal. After filtration the solution is evaporated to about half a volume and while stirring 1000 ml of isopropylether are added, the precipitated crystals are stirred for an hour in ice-water, washed with cold methanol and dried. Yield: 128 g (85%), m.p. 118°–120° C.

Proceeding according to the process described above applying the suitable compounds of the formula III and IV the following compounds of the formula II can be prepared:

(2-chloro-4-cyano-6-nitro-phenyl)-ethyl carbonate, yield 87%, m.p. 89° C.

(2-iodo-4-cyano-6-nitro-phenyl)-ethyl-carbonate, yield 92%, m.p. 112° C.

(2-bromo-4-cyano-6-nitro-phenyl)-isopropyl-carbonate, yield 87% m.p. 79° C.;

(2-bromo-4-cyano-6-nitro-phenyl)-ethyl-carbonate, yield 87.6%, m.p. 112° C.

2. Green house test comparing the compounds II.a. and Bromoxinyl

In culture dishes of 168 cm$^2$ basic area in sand we cultivated test plants for 20 days, whereafter the stocks were treated by sprinkling with the aqueous suspension of the formulated compositions.

14 days after the treatment the activity was evaluated. In the table the fresh weight of the plants is shown in the control's %.

| testing plant | compound II. a. (50 WP) 2 kg act. ingr./ha | Bromoxinyl (32 EC) 2 kg act. ingr./ha |
|---|---|---|
| maize | 100 | 67 |
| wheat | 100 | 68 |
| rye | 100 | 0 |
| millet | 100 | 0 |
| pea | 71 | 0 |
| garden larkspur | 0 | 0 |
| mustard | 0 | 0 |
| garden dittany | 0 | 0 |
| flax | 0 | 0 |
| milk thistle | 0 | 0 |
| sunflower | 0 | 0 |
| sorrel | 0 | 0 |
| tomato | 0 | 0 |

3. Lettuce root lengthening test

The small plants with roots of 5 mm of Latuca sativa germinated in the dark at 25° C. were transplanted in a CaSO$_4$ solution containing the substance to be tested in Petri-dishes (in every plate 4 ml of the solution and 15 plants). Thereafter the plants were exposed during 48 hours to variable exposure of 14 hours light, 10 hours dark period (average temperature 23° C.). Evaluation was by the growth of the root length expressed in the % of the untreated control.

| | $10^{-6}$ M | $10^{-5}$ M | $10^{-4}$ M |
|---|---|---|---|
| 3-bromo-5-nitro-4-hydroxy-benzo-nitrile | 88.8 | 95.4 | 10.1 |
| (2-bromo-4-cyano-6-nitro-phenyl-methyl-carbonate | 90.4 | 72.9 | 17.9 |
| (2-bromo-4-cyano-6-nitro-phenyl/-ethyl-carbonate | 90.5 | 87.7 | 3.7 |
| 3,5-dibromo-4-hydroxy-benzonitrile | 96.6 | 7.0 | 140.6 |
| (2,6-dibromo-4-cyano-phenyl)-ethyl-carbonate | 149.6 | 91.9 | 35.3 |

4. Measurement of the in vivo $CO_2$-fixation of wheat and spinach

The in invo $CO_2$ fixation of the leaves was determined by applying $^{14}CO_2$ according to Sárvári and coworkers (Physiol. Plant. 36: 187–192, 1976). The fixation finished the radioactivity of the leaves killed by heat treatment was measured by liquid scintillation technique. The data of the table are values expressed in the control's %.

| test compounds | spinach | wheat |
|---|---|---|
| 3.5-dibromo-4-hydroxy-benzonitrile | 10.7 | 47.4 |
| (2-bromo-4-cyano-6-nitro-phenyl)-methyl-carbonate | 11.0 | 91.0 |
| (2-bromo-4-cyano-6-nitro-phenyl)-phenyl-carbonate | 6.0 | 69.0 |
| (2-bromo-4-cyano-6-nitro-phenyl)-allyl-carbonate | 11.0 | 93.0 |

5. Preparation of (2-bromo-4-cyano-6-nitro-phenyl)-phenyl carbonate 121,5 g of 3-bromo-4-hydroxy-benzonitrile are dissolved in 650 ml of benzene and 73 ml of triethylamine are added. The solution obtained is reacted with the solution of 44 ml of chloro-formic acid phenyl-ester in 75 ml of benzene in about 30 minutes dropwise at 20°–25° C. Thereafter the mixture is stirred for 2 hours at 20°–25° C. and further for 1 hour at 55°–60° C., cooled, 100 ml of water are added. After separation of the layers the benzene solution is washed once more with 100 ml of water.

The washing water is once extracted with 50 ml of benzene.

The unified benzene solution is dried with anhydrous sodium sulphate and clarified with charcoal. After filtration the solution is evaporated to about half a volume and while stirring 1000 ml of isopropylether are added, the precipitated crystals are stirred for 1 hour in icewater, filtered, washed with cold methanol and dried. Yield 92%, m.p. 86° C.

Proceeding according to the process of example 5 the following esters were prepared:

2. (2-bromo-4-cyano-6-nitro-phenyl)-allyl carbonate, yield 87%, m.p. 87° C.,
3. (2-bromo-4-cyano-6-nitro-phenyl)-2-methoxy-ethyl carbonate, yield 85%, m.p. 100° C.
4. 6-(2-bromo-4-cyano-6-nitro-phenyl)-S-ethyl carbonate, yield 83%, m.p. 109° C.,
5. O-(2-bromo-4-cyano-6-nitro-phenyl)-N,N-dimethyl thiocarbamate, yield 95% m.p. 135° C.,
6. 2-chloro-4-cyano-6-nitro-phenyl-phenyl carbonate, yield 92%, m.p. 89° C.,
7. (2-bromo-4-cyano-6-nitro-phenyl)-phenyl carbonate, yield 92%, m.p. 86° C.

6. Green house test comparing the compounds II.b. and Bromoxinyl

The tests were carried out according to those set forth in example 2. In the table the fresh weight of the plants is shown in the control's %.

| B. testing plant | compound II. b. (50 WP) 2 kg act. ingr./ha | Bromoxinyl (32 EC) 2 kg act. ingr./ha |
| --- | --- | --- |
| maize | 100 | 67 |
| wheat | 100 | 68 |
| amaranth (*Amaranthus retroflexus*) | 18 | 20 |
| white mustard (*Sinapis alba*) | 0 | 0 |
| bristle-grass (*Seteria italica*) | 26 | 26 |
| knotweed (*Polygonum lagratifolium*) | 10 | 10 |

7. From the compound of the formula II the following powder spraying agent was formulated:

80 g of the active ingredient were prehomogenized and after adding 3 g of the sodium salt of the alkylnaphthalene sulphonic acid (Wettol NT 1), 5 g of the sodium salt of lignin sulphonic acid (Borresperse B) and 12 g of technical silicon dioxyde (Neuburg chalk) the mixture was ground below 10 microns.

8. According to example 4 a WP formulation of the following composition was prepared:

85 g of the active ingredient, 4 g of the sodium salt of alkyl-naphthalene sulphonic acid, 5 g of the sodium salt of lignin sulphonic acid, 1 g of carbamide, 5 g of sodium silicate.

9. From the compound of formula II the following suspension formulation emulsifyable in water was prepared: 50 g of the active ingredient were homogenized and after adding 5 g of the Ca salt of alkane sulphonic acid (Hoe S 1557) and 5 g of fatty alcohol polyglycolether (Genapol 0-050) the mixture was ground in a pearl mill.

10. Proceeding according to example 9 an emulsion suspension of the following composition was prepared: 50 g of the active ingredient, 4 g of Atlox 4851 (an anionic and non anionic tenside mixture), 6 g of Atlox 3400, 1 g of an organophil bentonite and 39 g of solvent naphtha.

What we claim is:

1. A compound of the formula (II)

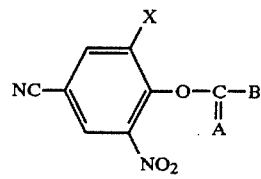

wherein

A is oxygen or sulfur;
B is O-$C_1$ to $C_4$ alkyl, O-$C_2$ to $C_6$ alkenyl, O-$C_6$ to $C_{10}$ aryl, O-$C_1$ to $C_4$ alkoxy-$C_1$ to $C_4$ alkyl, or S-$C_1$ to $C_4$ alkyl; and X is chloro, bromo or iodo.

2. The compound defined in claim 1 wherein X is bromo and A is oxygen.

3. (2-bromo-4-cyano-6-nitro-phenyl)-methyl carbonate as defined in claim 2.

4. A compound of the formula (II)

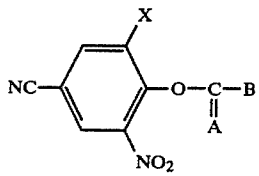

wherein

A is oxygen or sulfur;
B is O-$C_2$ to $C_6$ alkenyl, O-$C_6$ to $C_{10}$ aryl, or O-$C_1$ to $C_4$ alkoxy-$C_1$ to $C_4$ alkyl; and
X is chloro, bromo or iodo.

5. The compound defined in claim 4 wherein X is bromo and A is oxygen.

6. (2-bromo-4-cyano-6-nitro-phenyl)-phenyl-carbonate as defined in claim 5.

7. (2-bromo-4-cyano-6-nitro-phenyl)-allyl-carbonate as defined in claim 5.

8. A selective herbicidal composition which comprises 1 to 30% by weight of the compound of the formula (II) as defined in claim 1 along with at least one solid or liquid carrier or diluent, surface active agent or other auxiliary agent.

9. A selective herbicidal composition which comprises 1 to 30% by weight of the compound of the formula (II) as defined in claim 4 along with at least one solid or liquid carrier or diluent, surface active agent or other auxiliary agent.

10. A process for the selective weed control in grain or vegetable crops which comprises the step of postemergently administering to said crop and effective amount of the compound of the formula (II) defined in claim 1 in an amount of 1 to 5 kg/ha.

* * * * *